United States Patent [19]

Young

[11] Patent Number: 4,686,017
[45] Date of Patent: Aug. 11, 1987

[54] ELECTROLYTIC BATH AND METHODS OF USE

[75] Inventor: Donald C. Young, Fullerton, Calif.

[73] Assignee: Union Oil Co. of California, Los Angeles, Calif.

[21] Appl. No.: 750,322

[22] Filed: Jun. 28, 1985

[51] Int. Cl.$^4$ .............................................. C25D 3/00
[52] U.S. Cl. ................................ 204/45.1; 204/43.1; 204/46.1; 204/47; 204/47.5; 204/48; 204/49; 204/52.1; 204/53; 204/54.1; 204/55.1; 204/58.5; 204/129.85; 204/129.95; 427/319
[58] Field of Search ........... 204/129.95, 129.8, 129.85, 204/58.5, 52 R, 56 R, 56 M, 58, 43.1, 45.1, 46.1, 47, 47.5, 48, 49, 50.1, 53, 54.1, 55 R; 427/319

[56] References Cited

U.S. PATENT DOCUMENTS

| | | | |
|---|---|---|---|
| 1,340,708 | 5/1920 | Fjellanger | 71/28 |
| 1,903,860 | 4/1933 | Gockel | 204/46.1 |
| 2,458,839 | 1/1949 | Dyer et al. | 204/58.5 X |
| 2,549,411 | 4/1951 | Bell | 204/129.95 X |
| 2,712,524 | 7/1955 | Reichert | 204/129.95 |
| 2,712,525 | 7/1955 | Fischer | 204/129.95 X |
| 3,087,874 | 4/1963 | Greisl et al. | 204/129.95 |
| 3,772,167 | 11/1973 | Bharucha et al. | 204/44.5 |
| 4,116,644 | 9/1978 | Jones | 71/29 |
| 4,214,888 | 7/1980 | Young | 71/28 |
| 4,293,291 | 10/1981 | Canaris | 204/50 R |
| 4,310,343 | 1/1982 | Verdegaal et al. | 71/28 |
| 4,315,763 | 2/1982 | Stoller et al. | 71/29 |
| 4,384,930 | 5/1983 | Eckles | 204/44.4 |
| 4,397,675 | 8/1983 | Young | 71/28 |
| 4,402,852 | 9/1983 | Young | 252/182 |
| 4,404,116 | 9/1983 | Young | 252/182 |
| 4,445,925 | 5/1984 | Young | 71/28 |
| 4,447,253 | 5/1984 | Young | 71/28 |
| 4,482,444 | 11/1984 | Frass et al. | 204/129.35 |
| 4,488,942 | 12/1984 | Martin et al. | 204/44.2 |
| 4,512,813 | 4/1985 | Young | 134/27 |
| 4,522,644 | 6/1985 | Young | 71/78 |

FOREIGN PATENT DOCUMENTS

| | | | |
|---|---|---|---|
| 2154725 | 5/1973 | France | 204/58.5 |
| 313570 | 4/1956 | Switzerland | 204/129.95 |

OTHER PUBLICATIONS

Frederick A. Lowenheim, "Modern Electroplating", 3rd Edition, p. 63, (1978).
L. F. Yntema et al., J. American Chem. Soc., vol. 52, pp. 2693-2698, (1930).
R. D. Blue et al., Trans. Elec. Soc., vol. 43, pp. 231-238, (1933).
J. M. Kape, Plating, pp. 26-34, Jan. 1968.
Kirk-Othmer Encyclopedia of Chemical Technology, Third Edition, vol. 8, (pp. 826-869), John Wiley & Sons, 1979.
D. F. du Toit, Verslag Akad. Wetenschappen, 22, 573-574, (abstracted in Chemical Abstracts, 8, 2346, (1914).
L. H. Dalman, "Ternary Systems of Urea and Acids. I. Urea, Nitric Acid and Water, II. Urea, Sulfuric Acid and Water. III. Urea, Oxalic Acid and Water"; JACS, 56, 549-553, (1934).
Donald C. Young, application Ser. No. 442,296, filed Nov. 17, 1982; for Systemic Herbicidal Compositions and Methods of Use.
Donald C. Young, application Ser. No. 455,317, filed Jan. 3, 1983; for Plant Seed Compositions and Methods for Treating Plant Seeds.
Donald C. Young, application Ser. No. 455,268, filed Jan. 3, 1983, for Cellolosic Compositions and Methods for Treating Cellulosic Materials.
Donald C. Young, application Ser. No. 444,667, filed Nov. 26, 1982 for Methods for Controlling Vegetation.
Donald C. Young, application Ser. No. 674,359 filed Nov. 20, 1984 for Methods for Chemically Reducing Nitrogen Oxide Emissions.
Donald C. Young, application Ser. No. 673,508, filed Nov. 20, 1984 for Thermally Stable Urea-Sulfuric Acid Combinations and Methods of Manufacture.
Donald C. Young, application Ser. No. 675,774, filed Nov. 28, 1984 for Methods for Removing Obstructions from Conduits.
Donald C. Young, application Ser. No. 453,496, filed Dec. 27, 1982 for Acid-Catalyzed Reactions and Compositions for Use Therein.
Donald C. Young, application Ser. No. 688,689 filed Jan. 3, 1985 for Pesticidal Compositions and Methods for Controlling Pests.
Donald C. Young, application Ser. No. 679,235 filed Dec. 7, 1984 for Methods for Cleaning Materials.
Donald C. Young, application Ser. No. 771,259 filed Aug. 30, 1985 for Acid Catalysts and Methods of Use.

*Primary Examiner*—T. Tung
*Attorney, Agent, or Firm*—Michael H. Laird; Gregory F. Wirzbicki; Dean A. Sandford

[57] ABSTRACT

An electrolytic bath, suitable for depositing a metal on or removing a metal from a substrate is provided which comprises an anode and cathode, an acid having a $pK_a$ of about 6 or less, and a chalcogen-containing compound soluble in said bath and having the empirical formula

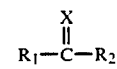

wherein X is a chalcogen, each of $R_1$ and $R_2$ is selected from hydrogen, $NR_3R_4$ and $NR_5$, at least one of $R_1$ and $R_2$ is other than hydrogen, each of $R_3$ and $R_4$ is hydrogen or a monovalent organic radical, and $R_5$ is a divalent organic radical, in which the molar ratio of the chalcogen compound to the acid is about 1 or more, and the molar ratio of water to the combination of acid and chalcogen compound is about 10 or less. The electrolytic bath enables the use of higher concentrations of strong acids than would otherwise be possible, minimize hydrogen and/or oxygen evolution at the electrodes with attendant advantages, and is useful in a variety of methods such as electroplating (including immersion plating), electroforming, electrolytic machining, electropolishing, electrolytic roughening, anodizing and electrowinning.

27 Claims, No Drawings

ELECTROLYTIC BATH AND METHODS OF USE

BACKGROUND OF THE INVENTION

1. Field of the Invention

This invention relates to electrolytic baths useful for depositing metals on or removing metals from substrates and to electrolytic methods using such baths.

2. Description of the Art

A variety of electrolytic methods are widely employed to deposit metals on or remove metals from conductive substrates for a variety of purposes. Electrolytic plating, including impressed current and sacrificial (immersion) plating, is used to produce decorative coatings of gold, silver, copper, chromium, nickel, or other metals on a variety of substrates. Plating is also employed to improve the corrosion resistance of corrosive substrates by depositing thin surface films of corrosion resistant metals such as zinc, tin, chromium, nickel and others. Wear resistant and friction modifying coatings of nickel, chromium, titanium, and other metals and their alloys are used to improve the wear resistance of bearing surfaces. Electroplating is also widely employed in the electronics industry to improve or modify the electrical properties of substrates such as contacts, printed circuits, electrical conductors, and other electrical apparatus in which specific surface or surface-to-substrate conductive properties are desired. Dissimilar metals are often electroplated onto metal surfaces to improve soldering characteristics or to facilitate subsequent coating by painting or application of other adhering films such as plastics, adhesives, rubber, etc.

Electroforming is a special application of electroplating in which usually thicker deposits are formed on a substrate which, typically, is later removed from the electroformed deposit. Such methods enable reproduction of fine detail in the substrate and are often used for the manufacture of templates for reproducing articles having fine surface features such as phonograph records Electrowinning processes represent another application of electroplating and are employed for the recovery of valuable metals from ores and scrap. Typically, the desired metal is first converted to an acid-soluble form such as the oxide by calcining the ore or scrap, after which the oxide is dissolved in an acid such as sulfuric, nitric, etc., and recovered from solution by electroplating.

Electrolytic metal removal is used for electrolytic machining, polishing, roughening and anodizing. Such processes involve placing the metal to be treated at the anode rather than the cathode and removing a portion of the metal from the article. Electrolytic machining usually involves masking a portion of the article's surface to expose only those portions to be removed, and it enables the rapid accurate machining of complex articles such as turbine blades and other machine parts. Electropolishing usually involves removal of metal from the cathode surface only at the high points of irregularities with little or no dissolution of metal at low points or valleys and is used to produce smooth lustrous finishes on metals such as stainless steel, carbon steel, brass, aluminum, silver, nickel, copper, zinc, chromium, and gold. In contrast to electropolishing, electrolytic roughening involves anodic treatment of a metal surface using special types of electric current such as an alternating current in which the current strength has an anode amplitude greater than the cathode amplitude. Such treatment unevenly removes metal from the anode surface and introduces or amplifies surface roughness on a microscopic scale. Illustrative electrolytic roughening processes are disclosed in U.S. Pat. No. 4,087,341 and are usually employed to improve surface adhesion and/or susceptibility to subsequent treatment such as anodizing. The latter treatment—anodizing—involves anodic metal removal combined with oxidation and is typically employed to provide a metal oxide coating to improve corrosion resistance, surface texture, adhesion to films or laminates, or modify electrical properties. Anodizing is typically carried out in aqueous acidic electrolytes which can contain various proportions of acids such as sulfuric, phosphoric, chromic, amidosulfonic, sulfosuccinic, sulfosalicylic acids and mixtures of these as disclosed in U.S. Pat. Nos. 4,482,444, 4,211,619, 4,049,504, and 4,229,266.

Many of the present electrolytic methods for depositing or removing metals involve the use of strong acid electrolytes, and others could be effected in the presence of strong acid electrolytes and/or higher acid concentrations could be employed if several of the problems associated with acid electrolytes could be overcome. Strong acids are ideal solvents for plating metal ions and compounds and for metal ions and compounds removed during anodic treatment. They are also highly conductive and therefore introduce little electrolyte resistance to current flow. However, current densities and cathode voltages required to effect the necessary cathodic reduction and/or anodic oxidation often exceed the hydrogen over-voltage potential at the cathode and/or the oxygen over-voltage potential at the anode, either of which can introduce significant complications into the process, detract from product quality, or, in severe cases, render electrolytic methods totally impractical. Cathode potentials which exceed the hydrogen over-voltage potential result in hydrogen evolution, irregular and/or non-adherent metal deposition, hydrogen embrittlement, especially with high strength steels, and amplify pre-existing differential potentials across the cathode surface. Cathode surface potential variations promote the problems referred to above, and accentuation of such potential difference exacerbates those problems. Hydrogen evolution and other factors associated with localized or general cathode voltages in excess of the hydrogen over-voltage potential also promote surface pitting, waste electrical energy and can create an explosion hazard.

Localized or general anodic voltages in excess of the oxygen over-voltage potential cause oxygen evolution at the anode, create local distortions in current flow, impair product quality, waste electrical energy, and can create a hazardous, explosive atmosphere. Another disadvantage associated with the use of strong acids in electrolytic processing involves the corrosivity of such acids for the treated substrate or coating.

Thus, the use of strong acids, particularly in high concentrations, is often avoided since such acids generally detract from the quality of the finished product and complicate process control. In particular, strong acids, especially when employed at high concentrations, diminish the homogeneity, brightness, and dimensional conformity of treated surfaces, reduce the tenacity of plated metals, waste energy in the production of hydrogen and/or oxygen, and, at best, limit the current density range and electrode voltages which can be employed.

A variety of steps have been employed to minimize or eliminate the negative effects of strong acid electrolytes including avoidance of strong acid electrolytes altogether, minimizing acid concentration, the addition of corrosion inhibitors and/or sophisticated leveling and/or brightening agents, limiting current density at the cathode and/or anode, or avoiding electrolytic treatment involving combinations of electrolytic baths and substrates when their use would be unacceptably expensive or impractical. For instance, sulfuric acid, one of the least expensive yet strongest mineral acids, is considered, by some authorities, as too corrosive to be used as an electrolyte for electrolytic machining as discussed in the Kirk Othmer Encyclopedia of Chemical Technology, Third Edition, Volume 8, John Wiley & Sons, pp. 751–763 (1979). Other investigators have sought to mitigate one or more of the disadvantages associated with strong acid electrolytes by the use of additives including surfactants, leveling and brightening agents, and corrosion inhibitors. Thus, urea is disclosed as a corrosion inhibitor in U.S. Pat. No. 4,482,444, for the electrolytic treatment of aluminum in a dilute sulfuric acid electrolyte. U.S. Pat. No. 4,488,942 discloses the use of thiourea to improve the crystal structure of zinc plate obtained in an acidic electroplating solution and to broaden the permissible current density range. Thiourea is also disclosed in combination with organic brighteners to facilitate cadmium plating from acidic baths in U.S. Pat. No. 4,293,391 and as a copper complexing agent for the immersion plating of tin on copper substrates in the presence of acidic electrolytes in the Kirk Othmer Encyclopedia of Chemical Technology, supra, page 859. Zinc electroplating baths involving acid-containing electrolytes, certain tertiary amine surfactants, and brightening agents including aldehydes, ketones, carboxylic acids, and certain pyridine compounds, are discussed in U.S. Pat. No. 4,384,930. Various leveling agents have also been disclosed such as condensation products of thiourea and aliphatic aldehydes (U.S Pat. No. 3,101,305) and condensation products of certain epihalohydrins and certain nitrogen-containing compounds such as substituted pyridines (U.S. Pat. No. 4,038,161).

All of the remedial procedures developed thus far suffer from one or more disadvantages. They typically require the use of relatively dilute acid electrolytes, the elimination of strong acids altogether, or relatively low current densities and/or electrode surface potentials. They also require the use of relatively expensive, often short-lived, additives such as the brightening and leveling agents and/or surfactants, some of which are referred to above.

SUMMARY OF THE INVENTION

It has now been discovered that the disadvantages associated with the use of strong acid electrolytes for the electrolytic deposition of metals on, or the removal of metals from, substrates can be minimized or eliminated by employing as the electrolyte bath, in contact with the involved anode and cathode, an acid having a $pK_a$ of about 6 or less, and chalcogen-containing compound soluble in the bath which has empirical formula

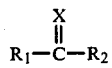

wherein X is a chalcogen, each of $R_1$ and $R_2$ is hydrogen, $NR_3R_4$ or $NR_5$, at least one of $R_1$ and $R_2$ being other than hydrogen, each of $R_3$ and $R_4$ is hydrogen or a monovalent organic radical and $R_5$ is a divalent organic radical, in which a molar ratio of the chalcogen-containing compound to the acid is about 1 or more, and the molar ratio of water to the combination of acid and chalcogen-containing compound is about 10 or less. Optionally, the bath may also contain one or more metal ions.

These electrolytic baths can be employed for the electrolytic deposition of a variety of metals on conductive substrates or for the electrolytic removal of metals from substrates. Thus, the methods of this invention involve the use of the described electrolytic baths for electroplating, including sacrificial (immersion) plating, electroforming, electrolytic machining, electropolishing, electrolytic roughening, anodizing, and electrowinning of metals. They enable the use of relatively strong acid electrolytes with their attendant advantages of high solvency and conductivity, minimize or eliminate the occurrence of cathode voltages in excess of the hydrogen over-voltage potential or anode voltages in excess of oxygen over-voltage potential, broaden permissible cathode and anode current densities, simplify the production of homogeneous, adherent plated surfaces (in electroplating and electroforming), minimize hydrogen embrittlement of cathode materials, reduce the occurrence and magnitude of surface voltage differentials at both the anode and cathode, and minimize or eliminate energy loss resulting from the formation of elemental hydrogen and/or oxygen.

DETAILED DESCRIPTION

Electrolytic baths are provided which are useful for depositing metal on or removing metal from a substrate and which contain an anode and cathode, an acid having a $pK_a$ of about 6 or less, and a chalcogen-containing compound soluble in the bath and having the empirical formula

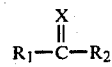

wherein X is a chalcogen, $R_1$ and $R_2$ are independently chosen from hydrogen, $NR_3R_4$ or $NR_5$, with at least one of $R_1$ and $R_2$ being other than hydrogen, $R_3$ and $R_4$ are independently chosen from hydrogen or a monovalent organic radical, and $R_5$ is a divalent organic radical, the molar ratio of the chalcogen-containing compound to the acid is about 1 or more, and the molar ratio of water to the combination of acid and chalcogen-containing compound is about 10 or less. Optionally, the bath may contain one or more metal ions. The described electrolytic baths can be employed in any process which involves depositing metal on or removing metal from a conductive substrate. Illustrative methods include electroplating, including sacrificial (immersion) plating, electroforming, electrolytic machining, electropolishing, electrolytic roughening, anodizing, and electrowinning of metals from scrap and ores.

The novel electrolytic baths and electrolytic treating methods enable the use of relatively concentrated strong acid electrolytes which have relatively high solvency and electrical conductivity. They thereby increase permissible solute concentrations while reducing electrolyte resistance and voltage drop. They minimize or eliminate the occurrence of cathode voltages in excess of the hydrogen over-voltage potential and anode voltages in excess of the oxygen over-voltage potential. In effect, the chalcogen-containing compound, when combined with the acid, broadens the differential between the voltage at which hydrogen begins to evolve at the cathode and the voltage at which the metal is reduced at and plated on the cathode. It also broadens the voltage differential between the point at which oxygen is evolved at the cathode and cathode metal is oxidized to soluble ion and removed.

The novel baths and methods also facilitate the formation of homogeneous adherent electroplated coatings, minimize or eliminate hydrogen embrittlement, especially in high strength steels, minimize the frequency and magnitude of differential potentials across both cathode and anode surfaces and thereby minimize problems associated with such potential variations. They thereby minimize the pitting and heterogeneity of electroplated surfaces, promote surface brightening and leveling, conserve energy and broaden the current density range at both the anode and cathode that can be employed in any given operation, and preserve the dimensional accuracy of electrolytically machined articles and surfaces.

Without intending to be constrained by any particular theory, it is presently believed that the various advantages associated with the electrolytic baths and the methods of this invention derive, at least in part, from attenuation of acid proton (hydrogen ion) lability due to association of the chalcogen-containing compound with the acid. The chalcogen-containing compound apparently combines with the acid to form an adduct as described in the case of urea and sulfuric acid in my U.S. Pat. No. 4,445,925, the disclosure of which is incorporated herein by reference in its entirety. The presence of the acid in the form of the adduct rather than as free acid apparently accounts for the observed improvements in the performance of electrolytic baths for depositing metals on or removing metals from conductive substrates. Thus, the concentration of chalcogen-containing compound should be equivalent at least to the strong acid concentration on a molar basis. Furthermore, the concentration of water in the electrolytic bath, or conversely the degree of dilution of the acid-chalcogen compound adduct, should not be so great as to promote dissociation of the adduct and the formation of appreciable free acid.

Various configurations of anode and cathode and various combinations of these elements can be employed in these methods. The number of anodes or cathodes and their configuration are not critical to the advantages achieved by the electrolytic baths of this invention although they, of course, do influence the accomplishment of some objectives such as electroforming and electrolytic machining as described in the available literature such as the Kirk Othmer Encyclopedia of Chemical Technology, pages 751-763 and the references cited therein, the disclosures of which are incorporated herein in their entireties. In fact, the anode and cathode can be combined into the same element as is the case in immersion plating.

The useful acids include strong organic and inorganic acids which have $pK_a$ values of about 6 or less, preferably about 3 or less. The strong mineral acids meeting this definition are presently preferred, the most preferred acids being sulfuric, nitric, pyrophosphoric, and hydrochloric acids and combinations of these with or without other acids. Minimum acid concentration is determined by the molar ratio of the chalcogen compound to the acid and the molar ratio of water to the combination of chalcogen compound and acid, while maximum acid concentration is prescribed by the minimum molar ratio of the chalcogen compound to the acid of about 1. Somewhat lower minimum acid concentrations can be employed in the presence of solvents, diluents or other additives other than water when such other additives are present in amounts sufficient to prevent the molar ratio of water to the combination of chalcogen compound and acid from significantly exceeding 10. Typically, acid concentrations will be at least about 10 weight percent, generally about 10 to about 70 weight percent, and preferably at least about 20 weight percent based on the total weight of additives (other than the anode and cathode).

In the chalcogen-containing compounds defined above, one of the monovalent radicals $R_3$ and $R_4$ can be hydrogen, and either or both of $R_3$ and $R_4$ can be any organic radical including alkyl, aryl, alkenyl, akenylaryl, aralkyl, aralkenyl, cycloakyl, cycloalkenyl, or alkynyl, which can be unsubstituted or substituted with pendant functional groups such as hydroxyl, carboxyl, oxide, thio, thiol, or others, and they can contain acyclic or cyclic heteroatoms such as oxygen, sulfur, nitrogen, or others. $R_5$ can be any divalent organic radical such as alkdyl, ardyl, alkenydyl, alkyndyl, aralkdyl, aralkendyl, which may contain pendant atoms or substituents and/or acyclic or cyclic heteroatoms as described for $R_3$ and $R_4$. Preferably, both $R_1$ and $R_2$ are other than hydrogen, both $R_3$ and $R_4$ are selected from hydrogen or hydrocarbyl radicals which, in combination, contain about 10 carbon atoms or less, and X is preferably oxygen. Such substituents are presently preferred due to their relatively higher chemical stability in the electrolytic baths of this invention. Particularly preferred chalcogen-containing compounds are urea, thiourea, formamide, and combinations of these.

The chalcogens are elements of Periodic Group VIB and include oxygen, sulfur, selenium, tellurium, and polonium. Oxygen and sulfur are presently preferred due to low cost, availability, low toxicity and chemical activity, and oxygen is the most preferred.

The minimum concentration of the chalcogen-containing compound is prescribed by the specified molar ratios for the respective components. Thus, it is defined by the requirement that the molar ratio of the chalcogen compound to the acid be at least about 1 and that the molar ratio of water to the combination of chalcogen compound and acid be about 10 or less. Typically, however, the chalcogen compound will be present at a concentration of at least about 10 weight percent, generally about 10 to about 80 weight percent, and preferably at least about 20 weight percent of the electrolytic bath (independent of the anode and cathode weights).

The chalcogen compound and strong acid are present in proportions corresponding to a molar ratio of the chalcogen compound to strong acid of at least about 1, generally about 1 to about 10, and molar ratios of about 1 to less than 5 can also be employed. When this molar ratio is 1, it appears that one molecule of chalcogen compound is adducted with each molecule of acid to form what is known as the mono-adduct. All of the strong acids form the mono-adduct with the described chalcogen compounds. Sulfuric acid, pyrophosphoric acid, and other acids which have two or more protons (hydrogen ions) which have pKa values of about 6 or less can adduct with two molecules of chalcogen compound for each molecule of acid to form the di-adduct. Proportions of chalcogen compound in excess of those required to completely complex the strong acid do not appear to produce any significant benefit other than to assure an adequate concentration of chalcogen compound should a portion of that compound be reacted and modified in the electrolyte bath. Furthermore, the attenuation of strong acid proton lability increases as the extent of adducting is increased in the case of acids, such as sulfuric acid, which will combine with more than one mole of chalcogen compound per mole of acid. Thus, the protonic acidity of sulfuric acid decreases as the chalcogen compound/acid molar ratio is increased from 1 to 2. Since significant reduction in protonic acidity can be achieved by formation of the mono-adduct (with attendant improvements in electrolyte properties), the presently preferred chalcogen compound/acid molar ratios are within the range of about 1 to less than 2, most preferably about 1 to about 1.5.

It also has been observed that the advantages realized by adducting the strong acid with the chalcogen compound diminish as the adduct is diluted with water. This effect becomes noticeable when the molar ratio of water to the combination of chalcogen compound and acid significantly exceed 2.5 and becomes excessive at molar ratios of about 10. Accordingly, the molar ratio of water to the combination of chalcogen compound and strong acid should be about 10 or less, preferably about 5 or less, and most preferably about 2.5 or less. In fact, substantially anhydrous combinations of chalcogen compound and adduct which contain about 1 weight percent water or less can be employed as electrolytes and are preferred in some cases. For instance, combination of urea and sulfuric acid which contain about 1 weight percent water or less are substantially more thermally stable than are such combinations which have higher water concentrations as discussed more fully in my copending application Ser. No. 673,508, filed Nov. 20, 1984, the disclosure of which is incorporated herein by reference in its entirety.

The chalcogen compound-acid combinations can be formed in situ in the electrolytic bath or they can be pre-formed by reaction of the chalcogen compound with the acid. However, such reactions are highly exothermic, and the reaction either must be conducted very slowly or adequate cooling must be provided to dissipate the heat of reaction, particularly when producing relatively concentrated compositions, to avoid exceeding the thermal decomposition temperature of the reactants or products. For instance, combinations of urea and sulfuric acid which have molar ratios below 2 begin to decompose at approximately 80° C. and decompose violently at about 90° C. and above. Methods for manufacturing such concentrated urea-sulfuric acid compositions while preventing thermal decomposition and the production of decomposition products are disclosed in my U.S. Pat. No. 4,445,925, supra. The methods disclosed in that patent can also be employed to manufacture other combinations of other strong acids and chalcogen-containing compounds useful in this invention.

In addition to the chalcogen-containing compound and acid components, the electrolytic bath may optionally contain one or more metal ions soluble in the bath such as titanium, zinc, chromium, nickel, aluminum, gold, silver, indium, iron, copper, lead, platinum, palladium, rhodium, ruthenium, iridium, osmium, tin, and various alloys of these and other metals including tin-cobalt, tin-zinc, tungsten-cobalt, gold-molybdenum, chromium-molybdenum, silver-rhenium, brass, bronze, various other gold alloys, lead-tin, nickel-iron, tin-nickel, etc. Such ions can be added to the electrolytic bath in the form of any acid-soluble organic or inorganic compound such as the oxide, hydroxide, sulfide, carbonate, sulfate, nitrate, chloride, acetate, etc. Additives known in the art as useful in electrolytic metal-treating processes such as brighteners, leveling agents, acids in addition to the strong acids discussed above, surfactants, organic and inorganic solvents and dispersants, chelating agents, conductive salts, and/or other adjuvants also may be present.

The described electrolytic baths can be employed to deposit one or more metals on or remove one or more metals from conductive substrates. Methods which involve deposition of one or more metals from an electrolytic bath include electroplating—both impressed current and sacrificial (immersion) plating, electroforming and electrowinning. Methods which involve metal removal from conductive substrates include electrolytic machining, electropolishing, electrolytic roughening, and electrolytic anodizing. The optimum conditions such as electrode current density and surface voltage, electrode spacing, current type, e.g., d.c., a.c. or both, bath temperature, exposure time, etc., are not critical to this invention since the advantages discussed above which flow from the use of the electrolytic baths of this invention are realized under any circumstances.

Typically, the electrolytic methods involve operating temperatures of 0° to 100° C., generally about 10° to about 80° C., particularly when aqueous electrolytes are employed. Temperatures of up to 200° C. or higher can be employed with the thermally stable, anhydrous electrolytic baths. Current densities are usually at least about 1, typically 1 to about 10,000, and most often 100 to about 2,000 amps per square foot (ASF). Electrode voltages are usually equivalent to or in excess of the over-voltage of the ion being plated on or removed from the electrode, preferably below the hydrogen and/or oxygen over-voltages, and are usually at least about 0.1, typically about 0.2 to about 1.3 volts. Contact times of at least about 1 minute are generally employed, and longer exposure times are required for greater degrees of metal deposition or removal as is the case in electroforming and electrolytic machining. Electroplating, electro-forming, electrowinning, electrolytic polishing and electrolytic machining typically employ only direct current while electrolytic roughening and anodizing can employ direct current or alternating current or a combination of both.

The substrate employed in plating, forming and electrowinning operations can be any electrically conductive metallic or non-metallic material such as plastic, leather, wood, plaster, rubber, glass and other ceramics, all conductive metals and alloys, including iron, chromium, nickel, copper, aluminum, magnesium, zinc, titanium, zirconium, tantalum, niobium, molybdenum, tungsten and alloys of these metals, especially the ferrous alloys such as mild steel, high carbon steel and stainless steels. The metals and metal alloys are typically employed as substrates in electrolytic polishing, machining, roughening, and anodizing.

Plating metals typically employed in electroplating, forming and electrowinning include all metal ions which are platable on a cathode and which are soluble in the electrolytic bath including, for example, titanium, zinc, chromium, nickel, aluminum, gold, silver, indium, iron, copper, lead, platinum, palladium, rhodium, ruthenium, iridium, osmium, tin, and various alloys of these and other metals including tin-cobalt, tin-zinc, tungsten-cobalt, gold-molybdenum, chromium-molybdenum, silver-rhenium, brass, bronze, various other gold alloys, lead-tin, nickel-iron, tin-nickel, etc.

Electroplating and electroforming conditions applicable to specific combinations of platable metals and substrates are discussed in Kirk Othmer Encyclopedia of Chemical Technology, supra, pages 826-869, in the references cited therein, and in U.S. Pat. Nos. 4,293,391 (cadmium-plating), 4,454,168 (copper-plating on printed circuits), 4,384,930 (electroplating of tin, lead, copper, zinc, cadmium, and tin-lead alloys), and 4,488,942 (zinc-plating), the disclosures of which are incorporated herein by reference in their entireties. Electrolytic machining conditions applicable to substrates of particular compositions and to the forming of specific shapes are discussed in the Kirk Othmer Encyclopedia of Chemical Technology, supra, at pages 751-763 and in the references cited therein, the disclosures of which are incorporated herein by reference in their entireties.

Several electropolishing applications (including electrolytic brightening) are discussed in the Kirk Othmer Encyclopedia of Chemical Technology, supra, Vol. 15 at page 303 and in the references cited therein, and electrolytic roughening and anodizing are discussed in U.S. Pat. No. 4,482,444, the disclosures of which are incorporated herein by reference in their entireties.

The invention is further described by the following Examples which are illustrative of specific modes of practicing the invention and are not intended as limiting the scope of the invention as defined by the appended claims.

EXAMPLE I

A urea-sulfuric acid adduct having urea/$H_2SO_4$ molar ratio of 1.06 and an $H_2O$/(urea plus $H_2SO_4$) molar ratio of 1.02, and containing 29 weight percent sulfuric acid, 32 weight percent urea, and 19 weight percent water is prepared by the methods described in my U.S. Pat. No. 4,445,925. Copper sulfate is added to the resulting adduct in an amount corresponding to 0.1 weight percent, and a mild steel plate is suspended in the electrode for two days at 100° F. No current is impressed on the system. This treatment produces a bright, homogeneous, adherent, pit-free copper plate over all exposed surfaces of the steel plate with no evidence of corrosion or non-adherent copper precipitate. Periodic inspection of the bath during the plating operation confirms the absence of any gas evolution.

EXAMPLE II

A rectangular mild steel cathode measuring 2 inches by 6 inches approximately ⅛-inch thick and having a total exposed surface of 24 square inches is suspended in the electrolyte described in Example I opposing a platinum gauge anode measuring 2 inches by 4 inches, and a potential difference of 10 volts is imposed across the electrodes to produce a current of 2 amps corresponding to 12 ASF for one hour. There is no evidence of hydrogen evolution at the cathode although minor oxygen evolution is observed at the anode.

This treatment results in a bright, homogeneous, adherent, pit-free copper plate over all surfaces of the cathode in the absence of any cathode corrosion.

EXAMPLE III

The operation described in Example II can be repeated with the exception that an electrolyte comprising 0.1 weight percent copper sulfate, 49 weight percent sulfuric acid, and 51 weight percent water can be substituted for the urea-sulfuric acid adduct described in Example I. Hydrogen evolution will be apparent at the mild steel cathode almost immediately following imposition of the 10 volt differential across the electrodes, and copper reduced to copper metal at the cathode would sluff off the steel plate and no adherent coating would be formed. Corrosive acid attack of the mild steel cathode would occur immediately upon immersion of the steel plate into the acid electrolyte.

While particular embodiments of this invention have been described, it will be understood, of course, that the invention is not limited thereto since many obvious modifications can be made, and it is intended to include within this invention any such modifications as will fall within the spirit and scope of the appended claims.

I claim:

1. A method for electrolytically plating a metal on an electrically conductive substrate which method comprises suspending said electrically conductive substrate as a cathode in an electrolytic cell comprising an anode and said cathode immersed in an electrolytic bath comprising sulfuric acid and a chalcogen-containing compound soluble in said bath and having the empirical formula:

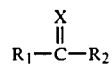

wherein X is a chalcogen, each of $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected from divalent organic radicals, the molar ratio of said chalcogen-containing compound to said sulfuric acid is about 1 to less than 5, and the molar ratio of water to the combination of said sulfuric acid and said chalcogen-containing compound is about 10 or less, and electrolyticaly plating said metal on said substrate.

2. The method defined in claim 1 wherein said chalcogen-containing compound comprises urea, the molar ratio of water to the combinsation of said urea and sulfuric acid is about 2.5 or less, said sulfuric acid constitutes at least 10 weight percent of said bath, and said urea constitutes at least about 10 weight percent of said bath.

3. The method defined in claim 1 wherein said chalocgen-containing compound comprises a member selected from the group consisting of urea, thiourea, formamide, and combinations thereof, and the molar ratio of water to the combination of said chalcogen-containing compound and said sulfuric acid is about 5 or less.

4. The method defined in claim 1 which further comprises the step of impressing a direct current voltage across said electrically conductive substrate and an anode, and said chalcogen is selected from the group consisting of oxygen, sulfur, and combinations thereof.

5. The method defined in claim 4 wherein said chalcogen-containing compound comprises a member selected from the group consisting of urea, thiourea, formamide, and combinations thereof, the molar ratio of said water to the combination of said chalcogen-containing compound and said sulfuric acid is about 5 or less, and said platable ions comprise ions of a metal selected from the group consisting of zinc, chromium, nickel, gold, silver, indium, iron, copper, lead, platinum, palladium, rhodium, ruthenium, iridium, osmium, tin and combinations thereof.

6. The method defined in claim 1 wherein said chalcogen-containing compound comprises urea, and said bath comprises less than about 1 weight percent water based on the combined weight of said sulfuric acid and said urea.

7. A method for electrolytically removing a metal from an electrically conductive substrate which method comprises employing said substrate as the anode in an electrolytic cell comprising said anode and a cathode immersed in an electrolytic bath comprising sulfuric acid and a chalcogen-containing compound soluble in said bath and having the empoirical formula:

wherein X is a chalcogen, each of $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected from divalent organic radicals, the molar ratio of said chalcogen-containing compound to said sulfuric acid is about 1 to less than 5, and the molar ratio of water to the combination of said sulfuric acid and said chalcogen-containing compound is about 10 or less, and impressing a voltage differential across said cathode and said anode.

8. The method defined in claim 7 wherein said chalcogen-containing compound comprises a member selected from the group consisting of urea, thiourea, formamide, and combinations thereof, and the molar ratio of water to the combination of said chalcogen-containing compound and said sulfuric acid is less than 5.

9. The method defined in claim 7 wherein the molar ratio of water to the combination of said chalcogen-containing compound and said sulfuric acid is about 2.5 or less.

10. The method defined in claim 7 which comprises electrolytic-machining said substrate.

11. The method defined in claim 7 which comprises electropolishing said substrate.

12. The method defined in claim 7 which comprises electro-roughening said substrate.

13. The method defined in claim 7 which comprises anodizing said substrate.

14. The method defined in claim 7 wherein said bath comprises less than 1 weight percent water based on the combined weight of said sulfuric acid and said chalcogen-containing compound.

15. A method for electrolytically plating a metal on an electrically conductive substrate, which method comprises suspending said electrically conductive substrate in an electrolytic bath which comprises at least about 10 weight percent sulfuric acid, at least about 10 weight percent of chalcogen-containing compound selected from the group consisting of urea, a formamide, thiourea, and combinations thereof, and a metal ion platable on said substrate wherein the molar ratio of said chalcogen-containing compound to said sulfuric acid is within the range of about 1 to less than 5, and the molar ratio of water to the combination of said chalcogen-containing compound and said sulfuric acid is about 10 or less, and electrolytically plating said platable ion on said substrate.

16. The method defined in claim 15 wherein said chalcogen-containing compound comprises urea.

17. The method defined in claim 15 wherein said platable ions comprise copper ions.

18. The method defined in claim 17 wherein said substrate comprises a ferrous metal.

19. A method for electrolytically depositing a metal on or removing a metal from a substrate which method comprises conducting said metal deposition or removal in an electrolytic bath comprising sulfuric acid and a chalcogen-containing compound soluble in said bath and having the empirical formula

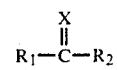

wherein X is S or O, each $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected for divalent orgnaic radicals, the molar ratio of said chalcogen-containing compound to said sulfuric acid is about 1 to less than 5, and the molar ratio of water to the combination of said sulfuric acid and said chalcogen-containing compound is about 10 or less.

20. A method for electrolytically depositing a metal on or removing a metal from a substrate which method comprises the step of conducting said metal deposition or removal in an electrolytic bath comprising sulfuric acid and a chalcogen-containing compound soluble in said bath and having the empirical formula

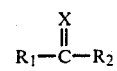

wherein X is S or O, each of $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected from divalent organic radicals, the molar ratio of said chalcogen-containing compound to said acid is about 1 to less than 2, and the molar ratio of water to the combination of said acid and said chalcogen-containing compound is about 2.5 or less.

21. A method for electrolytically depositing a metal on a substrate which comprises employing said substrate as a cathode in an electrolytic cell comprising an anode and said cathode immersed in an anhydrous, electrolytic bath comprising about 10 to about 70 weight percent sulfuric acid and a chalcogen-containing compound soluble in said bath and having the empirical formula

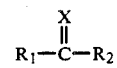

wherein X is a chalcogen, each of $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected from divalent organic radicals, the molar ratio of said chalcogen-containing compound to said acid being about 1 to less than 5, and depositing said metal on said substrate.

22. A method for electrolytically depositing a metal on a substrate which comprises employing said substrate as a cathode in an electrolytic cell comprising an anode and said cathode immersed in an anhydrous, electrolytic bath comprising about 10 to about 70 weight percent sulfuric acid and a compound selected from the group consisting of urea, thiourea, formamide, and combinations thereof in which the molar ratio of said compound to sulfuric acid is about 1 to less than 5, and depositing said metal on said substrate.

23. A method for electrolytically depositing aluminum or titanium on a substrate which method comprises suspending said substrate as a cathode in an electrolytic cell comprising an anode and said cathode immersed in an anhydrous, electrolytic bath comprising about 10 to about 70 weight percent sulfuric acid and a compound selected from the group consisting of urea, thiourea, formamide, and combinations thereof in which the molar ratio of said compound to sulfuric acid is within the range of about 1 to less than 5, and wherein said bath comprises a member selected from the group consisting of aluminum, titanium, and combinations thereof, and depositing said aluminum or titnium on said substrate.

24. A method for immersion plating platable metal ions on a substrate which comprises a metal which is less noble than said platable metal ions which method comprising suspending said substrate in an electrolyte containing said platable metal ions, sulfuric acid, and a chalcogen-containing compound soluble in said bath and having the empirical formula:

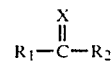

wherein X is a chalcogen, each of $R_1$ and $R_2$ is selected from hydrogen, $NR_3R_4$ and $NR_5$, at least one of $R_1$ and $R_2$ is other than hydrogen, each of $R_3$ and $R_4$ is selected from hydrogen and monovalent organic radicals, and $R_5$ is selected from divalent organic radicals, the molar ratio of said chalcogen-containing compound to said sulfuric acid is about 1 to less than 5, and the molar ratio of water to the combination of said sulfuric acid and said chalogen-containing compound is about 10 or less, under conditions sufficient to plate said metal ions on said substrate.

25. The method defined in claim 24 wherein the molar ratio of water to the combination of said chalcogen-containing compound and said sulfuric acid is about 5 or less, said chalcogen-containing compound comprises a member selected form the group consisting of urea, formamide, thiourea, and combinations thereof, and aid platable metal ions comprise ions selected from the group consisting of zinc, chromium, nickel, gold, silver, indium, iron, copper, lead, platinum, palladium, rhodium, ruthenium, irridium, osmium, tin, and combinations thereof.

26. The method defined in claim 24 wherein said chalcogen-containing compound comprises urea, and the molar ratio of water to the combination of said urea and sulfuric acid is about 2.5 or less.

27. The method defined in claim 24 wherein said chalcogen-containing compound comprises urea, the molar ratio of said urea to said sulfuric acid is about 1 to about 2, and the molar ratio of water to the combination of said urea and said sulfuric acid is about 5 or less.

* * * * *